US007585495B2

(12) United States Patent
O'Brien et al.

(10) Patent No.: US 7,585,495 B2
(45) Date of Patent: *Sep. 8, 2009

(54) METHOD FOR IDENTIFYING SHAMPOO-RESISTANT HAIR-BINDING PEPTIDES AND HAIR BENEFIT AGENTS THEREFROM

(75) Inventors: John P. O'Brien, Oxford, PA (US); Hong Wang, Kennett Square, PA (US); Antoinette E. Wilkins, Newark, DE (US); Ying Wu, Wallingford, PA (US)

(73) Assignee: E. I. Du Pont de Nemours and Company, Wilmington, DE (US)

( * ) Notice: Subject to any disclaimer, the term of this patent is extended or adjusted under 35 U.S.C. 154(b) by 177 days.

This patent is subject to a terminal disclaimer.

(21) Appl. No.: 11/251,715

(22) Filed: Oct. 17, 2005

(65) Prior Publication Data

US 2006/0073111 A1 Apr. 6, 2006

Related U.S. Application Data

(63) Continuation-in-part of application No. 10/935,642, filed on Sep. 7, 2004, now Pat. No. 7,220,405.

(60) Provisional application No. 60/501,498, filed on Sep. 8, 2003.

(51) Int. Cl.
*A61K 8/64* (2006.01)
*A61K 8/65* (2006.01)
*A61K 38/00* (2006.01)
*C12Q 1/68* (2006.01)
*A01N 37/18* (2006.01)

(52) U.S. Cl. ............................ 424/70.14; 435/6; 514/2
(58) Field of Classification Search ................... None
See application file for complete search history.

(56) References Cited

U.S. PATENT DOCUMENTS

| 4,416,873 A | 11/1983 | Puchalski et al. |
| 4,482,537 A | 11/1984 | El-Menshawy et al. |
| 5,192,332 A | 3/1993 | Lang et al. |
| 5,223,409 A | 6/1993 | Ladner et al. |
| 5,403,484 A | 4/1995 | Ladner et al. |
| 5,425,937 A | 6/1995 | Uchiwa et al. |
| 5,449,754 A | 9/1995 | Nishioka |
| 5,480,971 A | 1/1996 | Houghten et al. |
| 5,490,980 A | 2/1996 | Richardson et al. |
| 5,571,698 A | 11/1996 | Ladner et al. |
| 5,585,275 A | 12/1996 | Hudson et al. |
| 5,597,386 A | 1/1997 | Igarashi et al. |
| 5,639,603 A | 6/1997 | Dower et al. |
| 5,801,226 A | 9/1998 | Cummins et al. |
| 5,837,500 A | 11/1998 | Ladner et al. |
| 6,013,250 A | 1/2000 | Cannell et al. |
| 6,232,287 B1 | 5/2001 | Ruoslahti et al. |
| 6,267,957 B1 | 7/2001 | Green et al. |
| 6,280,747 B1 | 8/2001 | Philippe et al. |
| 6,344,443 B1 | 2/2002 | Liu et al. |
| 6,537,330 B1 | 3/2003 | Hoeffkes et al. |
| 6,620,419 B1 | 9/2003 | Lintner |
| 7,129,326 B2 * | 10/2006 | Janssen et al. ............... 530/329 |
| 2002/0098524 A1 | 7/2002 | Murray et al. |
| 2003/0152976 A1 | 8/2003 | Janssen et al. |
| 2003/0185870 A1 | 10/2003 | Grinstaff et al. |
| 2005/0050656 A1 | 3/2005 | Huang et al. |

FOREIGN PATENT DOCUMENTS

| CA | 2563999 A1 | 12/2005 |
| EP | 0 453 097 A2 | 10/1991 |
| EP | 0570583 A1 | 11/1993 |
| EP | 0634161 A1 | 1/1995 |
| JP | 02311412 A | 12/1990 |
| JP | 06065049 A | 3/1994 |
| JP | 08104614 A | 4/1996 |
| JP | 09003100 A | 1/1997 |
| JP | 2002363026 | 12/2002 |
| WO | WO 00/48558 | 8/2000 |
| WO | WO 01/07009 A1 | 2/2001 |
| WO | WO 01/45652 A1 | 6/2001 |
| WO | WO 01/79479 A2 | 10/2001 |
| WO | WO 02/065134 A2 | 8/2002 |
| WO | WO 03/031477 A1 | 4/2003 |
| WO | WO 03/102020 A2 | 12/2003 |
| WO | WO 04/000257 A2 | 12/2003 |
| WO | WO 2004/048399 A2 | 6/2004 |
| WO | WO 2004/069211 A2 | 8/2004 |
| WO | WO 2005/115306 A2 | 12/2005 |
| WO | WO 2006/097432 A2 | 9/2006 |
| WO | WO 2006/136607 A2 | 12/2006 |
| WO | WO 2007/060116 A2 | 5/2007 |
| WO | WO 2007/060117 A2 | 5/2007 |
| WO | WO 2007/063024 A2 | 6/2007 |

OTHER PUBLICATIONS

U.S. Appl. No. 11/074,473, filed Mar. 8, 2005, Huang et al.

(Continued)

*Primary Examiner*—Cecilia Tsang
*Assistant Examiner*—Marcela M Cordero Garcia

(57) ABSTRACT

A method for identifying shampoo-resistant hair-binding peptides is described. The shampoo-resistant hair-binding peptides bind strongly to hair from a shampoo matrix and are stable therein. Peptide-based benefit agents, such as peptide-based hair conditioners and hair colorants, based on the shampoo-resistant hair binding peptides are described. The peptide-based hair conditioners and hair colorants consist of a shampoo-resistant hair-binding peptide coupled to a hair conditioning agent or a coloring agent, respectively. Hair care and hair coloring product compositions comprising these peptide-based hair conditioners and colorants are also described.

22 Claims, No Drawings

OTHER PUBLICATIONS

U.S. Appl. No. 60/657,496, filed Mar. 1, 2005, Wang et al.

U.S. Appl. No. 60/657,494, filed Mar. 1, 2005, Wang et al.

S. G. Dixit et al., Combinatorial Chemistry—Principles and Practices, Journal of Scientific & Industrial Research, vol. 57:173-183, 1998.

Ronald H. Hoess, Protein Design and Phage Display, Chem. Rev., vol. 101:3205-3218, 2001.

Todd C. Holmes, Novel Peptide-Based Biomaterial Scaffolds for Tissue Engineering, Trends in Biotechnology, vol. 20(1):16-21, 2002.

Sandra R. Whaley et al., Selection of Peptides With Semiconductor Binding Specificity for Directed Nanocrystal Assembly, Nature, vol. 405:665-668, 2000.

Marc S. Reisch, Ingredients Makers Take Lessons From Biotechnology to Mastermind the Latest in Personal Care, C&EN Northeast News Bureau, pp. 16-21, 2002.

David J. Kemp et al., Direct Immunoassay for Detecting *Escherichia coli* Colinies That Contain Polypeptides Encoded by Cloned DNA Segments, PNAS, vol. 78(7):4520-4524, 1981.

Cheng-Ting Chien et al., The Two-Hybrid System: A Method to Identify and Clone Genes for Proteins That Interact With a Protein of Interest, PNAS, vol. 88:8578-9582, 1991.

David M. Helfman et al., Identification of Clones That Encode Chicken Tropomyosin by Direct Immunological Screening of a CDNA Expression Library, PNAS, vol. 80:31-35, 1983.

Maria Dani, Biological Libraries, J. of Receptor & Signal Transduction Research, vol. 21(4):447-468, 2001.

Genencor International, Bio Conference, San Francisco, CA, Jun. 8, 2004—Meeting Presentation, pp. 1-29.

Edward Dolk et al., Isolation of Llama Antibody Fragments for Prevention of Dandruff by Phage Display in Shampoo, Applied and Environmental Microbiology, vol. 71(1):442-450, 2005.

\* cited by examiner

```
                        SEQUENCE LISTING

<160> NUMBER OF SEQ ID NOS: 15

<210> SEQ ID NO 1
<211> LENGTH: 12
<212> TYPE: PRT
<213> ORGANISM: Artificial Sequence
<220> FEATURE:
<223> OTHER INFORMATION: Shampoo-resistant hair-binding peptide

<400> SEQUENCE: 1

Thr Pro Pro Glu Leu Leu His Gly Asp Pro Arg Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Shampoo-resistant hair-binding peptide

<400> SEQUENCE: 2

Thr Pro Pro Thr Asn Val Leu Met Leu Ala Thr Lys
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Shampoo-resistant hair-binding peptide

<400> SEQUENCE: 3

Asn Thr Ser Gln Leu Ser Thr
1               5

<210> SEQ ID NO 4
<211> LENGTH: 13
<212> TYPE: PRT
<213> ORGANISM: Artificial Sequence
<220> FEATURE:
<223> OTHER INFORMATION: Shampoo-resistant hair-binding peptide

<400> SEQUENCE: 4

Thr Pro Pro Glu Leu Leu His Gly Asp Pro Arg Ser Cys
1               5                   10
```

```
<210> SEQ ID NO 5
<211> LENGTH: 12
<212> TYPE: PRT
<213> ORGANISM: Artificial Sequence
<220> FEATURE:
<223> OTHER INFORMATION: Shampoo and hair conditioner-resistant
      hair-binding peptide

<400> SEQUENCE: 5

Gly Met Pro Ala Met His Trp Ile His Pro Phe Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Shampoo and hair conditioner-resistant
      hair-binding peptide

<400> SEQUENCE: 6

His Asp His Lys Asn Gln Lys Glu Thr His Gln Arg His Ala Ala
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: Shampoo and hair conditioner-resistant
      hair-binding peptide

<400> SEQUENCE: 7

His Asn His Met Gln Glu Arg Tyr Thr Asp Pro Gln His Ser Pro Ser
1               5                   10                  15

Val Asn Gly Leu
            20

<210> SEQ ID NO 8
<211> LENGTH: 20
<212> TYPE: PRT
<213> ORGANISM: Artificial Sequence
<220> FEATURE:
<223> OTHER INFORMATION: Shampoo and hair conditioner-resistant
      hair-binding peptide

<400> SEQUENCE: 8

Thr Ala Glu Ile Gln Ser Ser Lys Asn Pro Asn Pro His Pro Gln Arg
1               5                   10                  15

Ser Trp Thr Asn
            20

<210> SEQ ID NO 9
<211> LENGTH: 8
<212> TYPE: PRT
<213> ORGANISM: Artificial Sequence
<220> FEATURE:
<223> OTHER INFORMATION: Caspase cleavage site

<400> SEQUENCE: 9

Leu Glu Ser Gly Asp Glu Val Asp
1               5

<210> SEQ ID NO 10
<211> LENGTH: 37
<212> TYPE: PRT
```

```
<213> ORGANISM: Artificial Sequence
<220> FEATURE:
<223> OTHER INFORMATION: Peptide Spacer

<400> SEQUENCE: 10

Thr Ser Thr Ser Lys Ala Ser Thr Thr Thr Ser Ser Lys Thr Thr
1               5                   10                  15

Thr Thr Ser Ser Lys Thr Thr Thr Thr Ser Lys Thr Ser Thr Thr
            20                  25                  30

Ser Ser Ser Ser Thr
        35

<210> SEQ ID NO 11
<211> LENGTH: 22
<212> TYPE: PRT
<213> ORGANISM: Artificial Sequence
<220> FEATURE:
<223> OTHER INFORMATION: Peptide Spacer

<400> SEQUENCE: 11

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 12
<211> LENGTH: 10
<212> TYPE: PRT
<213> ORGANISM: Artificial Sequence
<220> FEATURE:
<223> OTHER INFORMATION: Peptide Spacer

<400> SEQUENCE: 12

Gly Pro Gly Gly Tyr Gly Pro Gly Gln Gln
1               5                   10

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccctcatagt tagcgtaacg                                           20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caagcctcag cgaccgaata                                           20

<210> SEQ ID NO 15
<211> LENGTH: 23
<212> TYPE: DNA
<213> ORGANISM: Artificial Sequence
<220> FEATURE:
<223> OTHER INFORMATION: Primer
```

```
<400> SEQUENCE: 15
cgtaacactg agtttcgtca cca                                                    23
```

METHOD FOR IDENTIFYING SHAMPOO-RESISTANT HAIR-BINDING PEPTIDES AND HAIR BENEFIT AGENTS THEREFROM

This patent application is a continuation in part of U.S. patent application Ser. No. 10/935,642, filed Sep. 7, 2004, incorporated herein by reference, which claims the benefit of U.S. Provisional Application 60/501,498, filed Sep. 8, 2003, now expired.

FIELD OF THE INVENTION

The invention relates to the field of personal care products. More specifically, the invention relates to a method for identifying shampoo-resistant hair-binding peptides and the use thereof in peptide-based hair benefit agents, such as hair conditioners and colorants.

BACKGROUND OF THE INVENTION

Hair conditioners, and hair colorants are well-known and frequently used hair care products. The major problem with current hair conditioners and non-oxidative hair dyes is that they lack the required durability for long-lasting effects. Oxidative hair dyes provide long-lasting color, but the oxidizing agents they contain cause hair damage. In order to improve the durability of these compositions, peptide-based hair conditioners, hair colorants, and other benefit agents have been developed (Huang et al., copending and commonly owned U.S. Patent Application Publication No.2005/0050656, and U.S. patent application Ser. No. 11/074,473). The peptide-based hair conditioners or colorants are prepared by coupling a specific peptide sequence that has a high binding affinity to hair with a conditioning or coloring agent, respectively. The peptide portion binds to the hair, thereby strongly attaching the conditioning or coloring agent. Peptides with a high binding affinity to hair have been identified using phage display screening techniques (Huang et al., supra; Estell et al. WO 0179479; Murray et al., U.S. Patent Application Publication No. 2002/0098524; Janssen et al., U.S. Patent Application Publication No. 2003/0152976; and Janssen et al., WO 04048399). The 0179479, 2002/0098524, 2003/0152976, and 04048399 applications describe contacting a peptide library with a hair sample in the presence of a dilute solution of bath gel (i.e., a 2% aqueous solution) and washing the phage-peptide-hair complex with the bath gel solution during phage display screening; however, the concentration of bath gel used is too low to identify bath gel-resistant hair-binding peptides. Additionally, the 04048399 application describes experiments done to determine the stability of phage peptide libraries in a 2% solution of shampoo. It was reported therein that the titer of the phage libraries incubated in the dilute shampoo solution for two hours decreased by two orders of magnitude. No shampoo resistant hair-binding peptides were described in that disclosure.

The hair-binding peptides have decreased binding affinity in the presence of a shampoo matrix and therefore do not bind strongly to hair from the shampoo matrix or are washed from the hair by the application of shampoo. Moreover, the hair-binding peptides are not stable for long periods of time in the shampoo matrix, which causes their binding affinity to decrease with time in a shampoo product.

Methods for identifying hair conditioner-resistant hair-binding peptides (Wang et al., copending and commonly owned U.S. Patent Application No. 60/657,496), skin care composition-resistant skin-binding peptides (Wang et al., copending and commonly owned U.S. Patent Application No. 60/657,494) and shampoo-resistant antibody fragments that bind to a cell surface protein of *Malassezia furfur* (Dolk et al., *Appl. Environ. Microbiol.* 71:442-450 (2005)) have been reported.

The problem to be solved, therefore, is to provide hair-binding peptides that are able to bind to hair from a shampoo matrix and are stable therein.

Applicants have solved the stated problem by discovering a method for identifying shampoo-resistant hair-binding peptides. The identified shampoo-resistant hair-binding peptide sequences bind to hair from a shampoo matrix. These hair-binding peptides may be used to prepare peptide-based hair benefit agents, such as conditioners and colorants, having improved binding affinity to hair in the presence of a shampoo and improved stability in shampoo compositions. Additionally, the shampoo-resistant peptide-based hair benefit agents may be more resistant to shampoo treatment.

SUMMARY OF THE INVENTION

The invention provides methods for the identification and isolation of new shampoo resistant hair binding peptides useful as linkers and adhesives in hair care compositions. The shampoo resistant hair binding peptides may be incorporated in di-block or tri-block structures optionally comprising chemical or peptide spacers and benefit agents. The methods of the invention rely on the screening of combinatorially generated peptide libraries for hair binding properties in the presence of a shampoo matrix.

Accordingly the invention provides a method for identifying a shampoo-resistant hair-binding peptide comprising:

a) providing a combinatorial library of DNA associated peptides;

b) contacting the library of (a) with a hair sample to form a reaction solution comprising DNA associated peptide-hair complexes;

c) isolating the DNA associated peptide-hair complexes of (b) from the reaction solution;

d) contacting the isolated DNA associated peptide-hair complexes of (c) with a shampoo matrix to form a peptide-hair complex-shampoo mixture wherein the concentration of the shampoo matrix is at least about 10% of the full strength concentration;

e) isolating the DNA associated peptide-hair complexes of (d) from the peptide-hair complex-shampoo mixture;

f) amplifying the DNA encoding the peptide portion of the DNA associated peptide-hair complexes of (e); and g) sequencing the amplified DNA of (f) encoding a shampoo-resistant hair-binding peptide wherein the shampoo-resistant hair-binding peptide is identified.

Optionally the method of the invention anticipates eluting the DNA associated peptides from the complexes with an eluting agent for further processing or identification.

In another embodiment the invention provides a shampoo-resistant hair-binding peptide identified by a process comprising the steps of:

a) providing a combinatorial library of DNA associated peptides;

b) contacting the library of (a) with a hair sample to form a reaction solution comprising DNA associated peptide-hair complexes;

c) isolating the DNA associated peptide-hair complexes of (b) from the reaction solution;

d) contacting the isolated DNA associated peptide-hair complexes of (c) with a shampoo matrix to form a peptide-hair complex-shampoo mixture wherein the concentration of the shampoo matrix is at least about 10% of the full strength concentration;

e) isolating the DNA associated peptide-hair complexes of (d) from the peptide-hair complex-shampoo mixture;

f) amplifying the DNA encoding the peptide portion of the DNA associated peptide-hair complexes of (e); and g) sequencing the amplified DNA of (f) encoding a shampoo-resistant hair-binding peptide wherein the shampoo-resistant hair-binding peptide is identified.

In a specific embodiment the invention provides a shampoo-resistant hair-binding peptide selected from the group consisting of SEQ ID NOs:1, 2, 3, 4, 5, 6, 7, and 8.

A diblock, peptide-based hair benefit agent having the general structure $(SRHBP_m)_n$-BA, is provided wherein;
 a) SRHBP is a shampoo-resistant hair-binding peptide;
 b) BA is a benefit agent;
 c) m ranges from 1 to about 100; and
 d) n ranges from 1 to about 50,000.

Similarly a triblock, peptide-based hair benefit agent having the general structure $[(SRHBP)_x-S_m]_n$-BA, is provided wherein;
 a) SRHBP is a shampoo-resistant hair-binding peptide;
 b) BA is a benefit agent;
 c) S is a spacer;
 d) x ranges from 1 to about 10;
 e) m ranges from 1 to about 100; and
 f) n ranges from 1 to about 50,000.

In other embodiments hair care product compositions are provided incorporating the di-block and tri-block peptide-based benefit agents described herein.

In an alternate embodiment the invention provides methods for coloring hair comprising applying the composition of the invention to the hair for a period of time sufficient to cause coloration of the hair.

Similarly the invention provides a method for coloring hair, eyebrows or eyelashes comprising the steps of:
 a) providing a hair coloring composition comprising a hair colorant selected from the group consisting of:
  i) $(SRHBP_m)_n$-C; and
  ii) $[(SRHBP)_x-S_m]_n$-C
  wherein:
   1) SRHBP is a shampoo-resistant hair-binding peptide;
   2) C is a coloring agent;
   3) n ranges from 1 to about 50,000;
   4) S is a spacer;
   5) m ranges from 1 to about 100; and
   6) x ranges from 1 to about 10;
  and wherein the shampoo-resistant hair-binding peptide is selected by a method comprising the steps of:
   A) providing a combinatorial library of DNA associated peptides;
   B) contacting the library of (A) with a hair sample to form a reaction solution comprising DNA associated peptide-hair complexes;
   C) isolating the DNA associated peptide-hair complexes of (B) from the reaction solution;
   D) contacting the isolated DNA associated peptide-hair complexes of (C) with a shampoo matrix to form a peptide-hair complex-shampoo mixture wherein the concentration of the shampoo matrix is at least about 10% of the full strength concentration;
   E) isolating the DNA associated peptide-hair complexes of (D) from the peptide-hair complex-shampoo mixture;
   F) amplifying the DNA encoding the peptide portion of the DNA associated peptide-hair complexes of (E); and
   G) sequencing the amplified DNA of (F) encoding a shampoo-resistant hair-binding peptide wherein the shampoo-resistant hair-binding peptide is selected; and
 b) applying the hair coloring composition of (a) to hair, eyebrows or eyelashes for a time sufficient for the hair colorant to bind to hair, eyebrows or eyelashes.

Alternatively the invention provides a method for forming a protective layer of a peptide-based conditioner on hair comprising the steps of:
 a) providing a hair care composition comprising a hair conditioner selected from the group consisting of:
  i) $(SRHBP_m)_n$-HCA; and
  ii) $[(SRHBP)_x-S_m]_n$-HCA
  wherein:
   1) SRHBP is a shampoo-resistant hair-binding peptide;
   2) HCA is a hair conditioning agent;
   3) n ranges from 1 to about 50,000;
   4) S is a spacer;
   5) m ranges from 1 to about 100; and
   6) x ranges from 1 to about 10;
  and wherein the shampoo-resistant hair-binding peptide is selected by a method comprising the steps of:
   A) providing a combinatorial library of DNA associated peptides;
   B) contacting the library of (A) with a hair sample to form a reaction solution comprising DNA associated peptide-hair complexes;
   C) isolating the DNA associated peptide-hair complexes of (B) from the reaction solution;
   D) contacting the isolated DNA associated peptide-hair complexes of (C) with a shampoo matrix to form a peptide-hair complex-shampoo mixture wherein the concentration of the shampoo matrix is at least about 10% of the full strength concentration;
   E) isolating the DNA associated peptide-hair complexes of (D) from the peptide-hair complex-shampoo mixture;
   F) amplifying the DNA encoding the peptide portion of the DNA associated peptide-hair complexes of (E); and
   G) sequencing the amplified DNA of (F) encoding a shampoo-resistant hair-binding peptide wherein the shampoo-resistant hair-binding peptide is selected; and
 b) applying the hair care composition of (a) to hair and allowing the formation of said protective layer.

BRIEF DESCRIPTION OF THE FIGURES AND SEQUENCE DESCRIPTIONS

The invention can be more fully understood from the following detailed description, and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-4 are the amino acid sequences of shampoo-resistant hair-binding peptides.

SEQ ID NOs:5-8 are the amino acid sequences of shampoo and hair conditioner-resistant hair-binding peptides.

SEQ ID NO:9 is the amino acid sequence of the Caspase cleavage site.

SEQ ID NOs:10-12 are the amino acid sequences of peptide spacers.

SEQ ID NO:13 is the nucleotide sequence of the oligonucleotide primer used to sequence phage DNA.

SEQ ID NOs:14 and 15 are the nucleotide sequences of the oligonucleotide primers used in Example 2.

DETAILED DESCRIPTION OF THE INVENTION

The invention provides a method for identifying shampoo-resistant peptide sequences that specifically bind to human hair with high affinity in the presence of a shampoo matrix. The identified shampoo-resistant hair-binding peptide sequences bind to hair from a shampoo matrix and are stable therein. These hair-binding peptides may be used to prepare peptide-based hair benefit agents, such as conditioners and colorants, having high binding affinity to hair in the presence of shampoo and improved stability in a shampoo composition. Additionally, the shampoo-resistant peptide-based hair benefit agents may be more resistant to shampoo treatment.

The following definitions are used herein and should be referred to for interpretation of the claims and the specification.

"SRHP" means shampoo-resistant hair-binding peptide.

"BA" means hair benefit agent"

"HCA" means hair conditioning agent.

"C" means hair coloring agent.

"S" means spacer.

The term "peptide" refers to two or more amino acids joined to each other by peptide bonds or modified peptide bonds.

The term "hair" as used herein refers to human hair, eyebrows, and eyelashes.

The phrase "shampoo-resistant hair-binding peptide" refers to a peptide that binds strongly to hair from a shampoo matrix and is stable therein.

The phrase "shampoo matrix" refers to a medium comprising a shampoo product, either undiluted or in diluted form, or a mixture comprising at least one component of a shampoo product, in addition, at least two components of a shampoo product. Components of shampoo products include, but are not limited to, surfactants, viscosity/foam stabilizers, pearlescent agents, viscosity adjusting agents/thickeners, conditioning agents, pH adjusting agents, refatting agents, proteins, preservatives, and fragrance.

The phrase "full strength concentration" refers to the concentration of the components as they occur in a shampoo product.

The phrase "hair conditioner matrix" refers to a medium comprising a hair conditioner product, either undiluted or in diluted form, or a mixture comprising at least one component of a hair conditioner product, in addition, at least two components of a hair conditioner product. Components of hair conditioner products include, but are not limited to, hair conditioning agents, antioxidants, preserving agents, fillers, surfactants, UVA and/or UVB sunscreens, fragrances, thickeners, wetting agents, and anionic, nonionic or amphoteric polymers; and dyes or pigments.

The term "benefit agent" is a general term referring to a compound or substance that may be coupled with a shampoo-resistant hair-binding peptide for application to hair to provide a cosmetic or dermatological effect. Benefit agents typically include conditioners, colorants, fragrances, and the like along with other substances commonly used in the personal care industry.

The terms "coupling" and "coupled" as used herein refer to any chemical association and includes both covalent and non-covalent interactions.

The term "peptide-hair complex" means structure comprising a peptide bound to a hair fiber via a binding site on the peptide.

The term "non-target" refers to a substrate for which peptides with a binding affinity thereto are not desired. For the selection of shampoo-resistant hair-binding peptides, non-targets, include, but are not limited to, skin and plastic.

The term "nanoparticles" are herein defined as particles with an average particle diameter of between 1 and 100 nm. Preferably, the average particle diameter of the particles is between about 1 and 40 nm. As used herein, "particle size" and "particle diameter" have the same meaning. Nanoparticles include, but are not limited to, metallic, semiconductor, polymer, or other organic or inorganic particles.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer.

Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is Understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

The term "DNA associated peptide-hair complexes" refers to a complex between hair and a peptide where the peptide has associated with it an identifying nucleic acid component. Typically, the nucleic acid that is associated with peptide is produced as a result of a display system such as phage display. In this system, peptides are displayed on the surface of the phage while the DNA encoding the peptides is contained within the attached glycoprotein coat of the phage. The association of the coding DNA within the phage may be used to facilitate the amplification of the coding region for the identification of the peptide.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The invention provides a method for identifying shampoo-resistant peptide sequences that bind specifically to hair with high affinity in the presence of a shampoo matrix. The method is a modification of standard biopanning techniques wherein hair is contacted with a combinatorially generated library of peptides. Within the context of the present invention the resulting phage-peptide-hair complex is contacted with a shampoo matrix for a period of time. The phage-peptide-hair complex is isolated and optionally contacted with an eluting agent to give eluted phage-peptides and phage-peptides that remain bound to the hair. The eluted phage-peptides and/or the remaining bound phage-peptides are amplified and identified. The identified shampoo-resistant hair-binding peptide sequences may be used to construct peptide-based benefit agents, such as hair conditioners and hair colorants.

Identification of Shampoo-Resistant Hair-Binding Peptides

Shampoo-resistant hair-binding peptides (SRHBPs), as defined herein, are peptide sequences that specifically bind to hair from a shampoo matrix and are stable therein. The shampoo-resistant hair-binding peptides of the invention are from about 7 amino acids to about 45 amino acids in length, more preferably, from about 7 amino acids to about 25 amino acids in length, most preferably from about 7 to about 20 amino acids in length.

Suitable shampoo-binding peptide sequences may be selected using methods that are well known in the art. The peptides of the present invention are generated randomly and then selected against a hair sample based upon their binding affinity for the hair in the presence of a shampoo matrix, as described below. The generation of random libraries of peptides is well known and may be accomplished by a variety of techniques including, bacterial display (Kemp, D. J.; *Proc. Natl. Acad. Sci. USA* 78(7):45204524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (U.S. Pat. Nos. 5,449,754, 5,480,971, 5,585,275, and 5,639,603), and phage display technology (U.S. Pat. Nos. 5,223,409, 5,403,484, 5,571,698, and 5,837,500). Techniques to generate such biological peptide libraries are well known in the art. Exemplary methods are described in Dani, M., *J. of Receptor & Signal Transduction Res.*, 21 (4):447-468 (2001), Sidhu et al., *Methods in Enzymology* 328:333-363 (2000), and *Phage Display of Peptides and Proteins, A Laboratory Manual*, Brian K. Kay, Jill Winter, and John McCafferty, eds.; Academic Press, NY, 1996. Additionally, phage display libraries may be purchased from commercial sources, such as New England Biolabs Inc. (Beverly, Mass.).

In one embodiment it is particularly useful to have the DNA encoding the peptide associated with the peptide in some manner. This association facilitates rapid identification of the binding peptide in the screening or biopanning process. The coding DNA may be either PCR amplified or used to infect a replicating host to increase the expression of the peptide for facile identification. Typically DNA associated peptides are produced by the methods of phage display, bacteria display and yeast display as referenced above.

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

The shampoo-resistant hair-binding peptides of the invention may be identified using phage display by selecting phage peptides against a hair sample based upon their binding affinity for the hair in the presence of a shampoo matrix. The hair and the phage peptides may be contacted with the shampoo matrix in various ways to form a peptide-hair complex-shampoo mixture, as described in detail below. For example, the phage peptide library may be dissolved in the shampoo matrix which is then contacted with the hair sample. Alternatively, the phage-peptide-hair complex, formed by contacting the hair sample with the phage display library, may be subsequently contacted with a shampoo matrix. Additionally, a combination of these shampoo contacting methods may be used.

After a suitable library of phage-peptides has been generated or purchased from a commercial supplier, the library is contacted with an appropriate amount of hair sample to form a reaction solution comprising peptide-hair complexes. Human hair samples are available commercially, for example from International Hair Importers and Products (Bellerose, N.Y.), in different colors, such as brown, black, red, and blond, and in various types, such as African-American, Caucasian, and Asian. Additionally, the hair samples may be treated, for example using hydrogen peroxide to obtain bleached hair. The library of phage-peptides is dissolved in a suitable solution for contacting the hair sample. In one embodiment, the library of phage-peptides is dissolved in a buffered aqueous saline solution containing a surfactant. A suitable solution is Tris-buffered saline (TBS) with 0.5% Tween® 20. In another embodiment, the library of phage-peptides is dissolved in a shampoo matrix and then contacted with the hair sample. The solution containing the phage-peptide library may be agitated by any means in order to increase the mass transfer rate of the phage-peptides to the hair surface, thereby shortening the time required to attain maximum binding. The time required to attain maximum binding varies depending on a number of factors, such as size of the hair sample, the concentration of the peptide library, and the agitation rate. The time required can be determined readily by one skilled in the art using routine experimentation. Typically, the contact time is 1 minute to one hour. Optionally, the phage display library may be contacted with a non-target, such as skin or plastic, either prior to or simultaneously with contacting the hair sample to remove the undesired phage-peptides that bind to the non-target.

Upon contact with the hair sample, a number of the randomly generated phage-peptides bind to the hair to form a phage-peptide-hair complex. A number of peptides remain uncomplexed and portions of the hair sample are also unbound. Uncomplexed peptides may optionally be removed by washing using any suitable buffer solution, such as Tris-HCl, Tris-buffered saline, Tris-borate, Tris-acetic acid, triethylamine, phosphate buffer, and glycine-HCl, wherein Tris-buffered saline solution is preferred. The wash solution may also contain a surfactant such as SDS (sodium dodecyl sulfate), DOC (sodium deoxycholate), Nonidet P-40, Triton X-100, and Tween® 20, wherein Tween® 20 at a concentration of 0.5% is preferred.

After the uncomplexed material is removed, the phage-peptide-hair complex is contacted with a shampoo matrix for a period of time, typically, about 1 minute to about 30 minutes, to form a peptide-hair complex-shampoo mixture. A shampoo matrix, as used herein, refers to a medium comprising a shampoo product, either undiluted or in diluted form, or a mixture comprising at least one component of a shampoo product, in a addition, at least two components of a shampoo product. Components of shampoo product compositions are well-known in the art and are described below. Additionally, commercially available shampoo products, such as Dove® Extra Volume Shampoo (Unilever), Pantene Pro V (Proctor and Gamble), Herbal Essence (Clairol), Finesse (Helene Curtis), and Tresemme (Alberto Culver) may be used. Hair shampoos may be purchased at local supermarkets and pharmacies. Preferably, the shampoo matrix in which the shampoo-resistant hair-binding peptide will ultimately be employed, is used in the method. The shampoo matrix may be used undiluted or may be diluted to facilitate its application, particularly in the case of a very viscous composition. The shampoo matrix may be diluted with water or a suitable buffer solution, such as that described above, may be used. The concentration of the shampoo matrix is at least about 10%, in addition at least about 30%, in addition at least about 50%, and in addition at least about 75% of the full strength concentration of the shampoo product. Alternatively, the shampoo matrix may be used in undiluted form. Optionally the phage-peptide-hair complex may be contacted with the shampoo matrix one or more times The phage-peptide hair complex is removed from the phage-peptide-hair complex-shampoo mixture and is optionally washed one or more times using a buffer solution, as described above. The phage-peptide-hair complex is then contacted with an eluting agent, preferably after being transferred to a new container, to dissociate the phage-peptide from the hair; however, some of the phage-peptide may still remain bound to the hair after this treatment. The eluting agent may be any known eluting agent including, but not limited to, acid (pH 1.5-3.0); base (pH 10-12.5); salt solutions containing high salt concentrations such as $MgCl_2$ (3-5 M) and LiCl (5-10 M); water; ethylene glycol (25-50%); dioxane (5-20%); thiocyanate (1-5 M); guanidine (2-5 M); and urea (2-8 M), wherein treatment with an acid is preferred. If the elution buffer used is an acid or base, then, a neutralization buffer is added to adjust the pH to the neutral range. Any suitable buffer may be used, wherein 1 M Tris-HCl pH 9.2 is preferred for use with an acid elution buffer.

The eluted phage-peptides or the remaining bound phage-peptides, or both the eluted phage-peptides and the remaining bound phage-peptides are then amplified using methods known in the art. For example, the eluted phage-peptides and the remaining bound phage-peptides may be amplified by infecting/transfecting a bacterial host cell, such as E. coli ER2738, as described by Huang et al., supra with DNA encoding the desired peptide. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™ (3,4-cyclohexenoesculetin-β-D-galactopyranoside). After growth, the plaques are picked for DNA isolation and sequencing to identify sequences encoding the shampoo-resistant hair-binding peptide sequences. Alternatively, the eluted phage-peptides and the remaining bound phage-peptides may be amplified using a nucleic acid amplification method, such as the polymerase chain reaction (PCR). In this approach, PCR is carried out on the DNA encoding the eluted phage-peptides and/or the remaining bound phage-peptides using the appropriate primers, as described by Janssen et al. in U.S. Patent Application Publication No. 2003/0152976, which is incorporated herein by reference.

In one embodiment, the eluted phage-peptides and the remaining bound phage-peptides are amplified by infecting a bacterial host cell with DNA encoding the desired peptides, the amplified phage-peptides are contacted with a fresh hair sample, and the entire process described above is repeated one or more times to obtain a population that is enriched in shampoo-resistant hair-binding phage-peptides. After the desired number of biopanning cycles, the amplified phage-peptide sequences are determined using standard DNA sequencing techniques that are well known in the art to identify the shampoo-resistant hair-binding peptide sequences.

Shampoo-resistant hair-binding peptides have been identified using the above methods. Specifically, binding peptides, given as SEQ ID NOs:1-4, were isolated that have a high affinity for hair from a shampoo matrix and are stable therein.

Additionally, hair-binding peptides that are both shampoo and hair conditioner resistant may be identified using a combination of the method described above and the method to identify hair conditioner resistant hair-binding peptides, described by Wang et al. (copending and commonly owned U.S. Patent Application No. 60/657,496). In the combined method, the hair and peptide library is contacted with both a shampoo matrix and a hair conditioner matrix.

A hair conditioner matrix, as used herein, refers to a medium comprising a hair conditioner product, either undiluted or in diluted form, or a mixture comprising at least one component of a hair conditioner product, in a addition, at least two components of a hair conditioner product. Suitable hair conditioner product compositions are well-known in the art. Components of hair conditioner product compositions are described by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, the hair conditioner composition can be an aqueous solution, an aqueous-alcoholic solution, and a water-in-oil (W/O) or a oil-in-water (O/W) emulsion. Additionally, the hair conditioner composition may contain one or more conventional cosmetic or dermatological additives or adjuvants including but not limited to, hair conditioning agents (see below for examples), antioxidants, preserving agents, fillers, surfactants, UVA and/or UVB sunscreens, fragrances, thickeners, wetting agents and anionic, nonionic or amphoteric polymers, and dyes or pigments. These adjuvants are well known in the field of cosmetics and are described in many publications, for example see *Harry's Book of Cosmeticology*, $8^{th}$ edition, Martin Rieger, ed., Chemical Publishing, New York (2000). Additionally, commercially available hair conditioner compositions, such as Dove® Extra Volume Conditioner (Unilever), Pantene Pro V (Proctor and Gamble), Herbal Essence (Clairol), Finesse (Helene Curtis), and Tresemme (Alberto Culver) may be used. Hair conditioners may be purchased at local supermarkets and pharmacies. Preferably, the hair conditioner matrix in which the hair conditioner-resistant hair-binding peptide will ultimately be employed, is used in the method. The hair conditioner composition may be used undiluted or may be diluted to facilitate its application, particularly in the case of a very viscous composition. The hair conditioner matrix may be diluted with water or a suitable buffer solution, such as that described above, may be used. The concentration of the hair conditioner matrix is at least about 10%, preferably at least about 20% to about 50%, more preferably at least about 75% of the full strength concentration. Most preferably, the hair conditioner matrix is used in undiluted form.

The hair and the phage peptide library may be contacted with a shampoo matrix and a hair conditioner matrix in various ways. For example, the phage peptide library may be dissolved in either the shampoo matrix or the hair conditioner matrix which is then contacted with the hair sample, as described above. Then the phage-peptide-hair complex formed may be optionally washed, as described above, and then contacted with the other matrix. Additionally, the hair may be contacted with the phage-peptide library, which is dissolved in a suitable buffer, as described above. Then the resulting phage-peptide-hair complexes may be contacted with a shampoo matrix, as described above. The phage-peptide-hair complexes may optionally be washed and then contacted with a hair conditioner matrix. Alternatively, the phage-peptide-hair complexes may first be contacted with a hair conditioner matrix, followed by contacting with a shampoo matrix. In all the above methods, the remaining phage-peptide-hair complexes are contacted with an eluting agent, amplified, and identified as described above.

Shampoo and hair conditioner-resistant hair-binding peptides have been identified using the methods described above (see Example 3). The amino acid sequences of these shampoo and hair conditioner-resistant hair-binding peptides are given as SEQ ID NOs:5-8.

Production of Shampoo-Resistant Hair-Binding Peptides

The shampoo-resistant hair-binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the shampoo-resistant hair-binding peptides of the present invention may be prepared using recombinant DNA and molecular cloning techniques. Genes encoding the shampoo-resistant hair-binding peptides may be produced in heterologous host cells, particularly in the cells of microbial hosts, as described by Huang et al. (copending and commonly owned U.S. Patent Application Publication No. 2005/0050656).

Peptide-Based Hair Benefit Agents

The peptide-based hair benefit agents of the invention are formed by coupling a shampoo-resistant hair-binding peptide (SRHBP) with a benefit agent (BA), such as a conditioner, colorant, fragrance, and the like. The shampoo-resistant hair-binding peptide part of the conditioner binds strongly to the hair from a shampoo matrix, thus keeping the benefit agent attached to the hair for a long lasting conditioning effect. The coupling interaction between the shampoo-resistant hair-binding peptide and the benefit agent may be a covalent bond or a non-covalent interaction and may be through an optional spacer, as described below.

It may also be desirable to have multiple shampoo-resistant hair-binding peptides coupled to the benefit agent to enhance the interaction between the peptide-based hair conditioner and the hair, as described by Huang et al., (copending and commonly owned U.S. Patent Application Publication No.2005/0050656). This may be done by coupling multiple copies of single shampoo-resistant hair-binding sequences to the benefit agent or by linking two or more shampoo-resistant hair-binding peptide sequences together, either directly or through a spacer, and coupling the resulting multi-copy hair-binding sequence to the benefit agent. Additionally, multiple copies of the multi-copy shampoo-resistant hair-binding peptide sequence may be coupled to the benefit agent. In all these peptide-based hair benefit agents, multiple copies of the same shampoo-resistant hair-binding peptide or a combination of different shampoo-resistant hair-binding peptides may be used.

In one embodiment of the present invention, the peptide-based benefit agents are diblock compositions consisting of a shampoo-resistant hair-binding peptide (SRHBP) and a benefit agent (BA), having the general structure $(SRHBP_m)_n$-BA, where m ranges from 1 to about 100, preferably from 1 to about 10. When the benefit agent is a molecular species, n ranges from 1 to about 100, preferably from 1 to about 10. When the benefit agent is a particle, such as a pigment, n ranges from 1 to about 50,000, preferably from 1 to about 10,000.

In another embodiment, the peptide-based benefit agents contain a spacer (S) separating the shampoo-resistant hair-binding peptide from the benefit agent. Multiple copies of the shampoo resistant hair-binding peptide may be coupled to a single spacer molecule. Alternatively, multiple copies of shampoo-resistant hair-binding peptides may be separated by various spacers. In this embodiment, the peptide-based benefit agents are triblock compositions consisting of a shampoo-resistant hair-binding peptide, a spacer, and a benefit agent, having the general structure $[(SRHBP)_x-S_m]_n$-BA, where x ranges from 1 to about 10, preferably x is 1, and m ranges from 1 to about 100, preferably from 1 to about 10. When the benefit agent is a molecular species, such as a dye or non-particle conditioning agent, n ranges from 1 to about 100, preferably from 1 to about 10. When the benefit agent is a particle, such as a pigment, n ranges from 1 to about 50,000, preferably from 1 to about 10,000.

It should be understood that as used herein, SRHBP is a generic designation and is not meant to refer to a single shampoo-resistant hair-binding peptide sequence. Where m or x as used above, is greater than 1, it is well within the scope of the invention to provide for the situation where a series of hair binding peptides of different sequences may form a part of the composition. Additionally, it should be understood that these structures do not necessarily represent a covalent bond between the peptide, the benefit agent, and the optional spacer. As described below, the coupling interaction between the peptide, the hair conditioning agent, and the optional spacer may be either covalent or non-covalent.

The preparation of the shampoo-resistant peptide-based benefit agents of the invention is described below for hair conditioner and hair colorants. It should be understood that these methods may be applied to other benefit agents and that these other shampoo-resistant peptide-based benefit agents are within the scope of the invention.

Peptide-Based Hair Conditioners

The peptide-based hair conditioners of the invention are formed by coupling a shampoo-resistant hair-binding peptide (SRHBP) with a hair conditioning agent (HCA). The shampoo-resistant hair-binding peptide part of the conditioner binds strongly to the hair from a shampoo matrix, thus keeping the conditioning agent attached to the hair for a long lasting conditioning effect. The shampoo-resistant hair-binding peptides are selected by the methods described above, and include, but are not limited to, the hair-binding peptide sequences given as SEQ ID NOs:1-8.

Hair conditioning agents as herein defined are agents which improve the appearance, texture, and sheen of hair as well as increasing hair body or suppleness. Hair conditioning agents, include, but are not limited to, styling aids, hair straightening aids, hair strengthening aids, and volumizing agents, such as nanoparticles. In the peptide-based hair conditioners of the present invention, any suitable hair conditioning agent may be used. Hair conditioning agents are well known in the art, see for example Green et al. (WO 0107009), incorporated herein by reference, and are available commercially from various sources. Suitable examples of hair conditioning agents include, but are not limited to, cationic polymers, such as cationized guar gum, diallyly quaternary ammonium salt/acrylamide copolymers, quaternized polyvinylpyrrolidone and derivatives thereof, and various polyquaternium-compounds; long chain alkyl groups (i.e., $C_8$ to $C_{24}$); cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as aminodimethicone; and nanoparticles, such as silica nanoparticles and polymer nanoparticles. The preferred hair conditioning agents of the present invention contain amine or hydroxyl functional groups to facilitate coupling to the hair-binding peptides, as described below. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

The peptide-based hair conditioners of the present invention are prepared by coupling a specific shampoo-resistant hair-binding peptide to a hair conditioning agent, either directly or via an optional spacer. The coupling interaction may be a covalent bond or a non-covalent interaction, such as hydrogen bonding, electrostatic interaction, hydrophobic interaction, or Van der Waals interaction. In the case of a non-covalent interaction, the peptide-based hair conditioner may be prepared by mixing the peptide with the conditioning agent and the optional spacer (if used) and allowing sufficient time for the interaction to occur. The unbound materials may be separated from the resulting peptide-based hair conditioner adduct using methods known in the art, for example, gel permeation chromatography.

The peptide-based hair conditioners of the invention may also be prepared by covalently attaching a specific shampoo-resistant hair-binding peptide to a hair conditioning agent, either directly or through a spacer, as described by Huang et al., (copending and commonly owned U.S. Patent Application Publication No.2005/0050656).

Any suitable known peptide or protein conjugation chemistry may be used to form the peptide-based conjugates used in the invention. Conjugation chemistries are well-known in the art (see for example, Hermanson, *Bioconjugate Techniques*, Academic Press, New York (1996)). Suitable coupling agents include, but are not limited to, carbodiimide coupling agents, acid chlorides, isocyanates, epoxides, maleimides, and other functional coupling reagents that are reactive toward terminal amine and/or carboxylic acid terminal groups, and sulfhydryl groups on the peptides. Additionally, it may be necessary to protect reactive amine or carboxylic acid groups on the peptide to produce the desired structure for the peptide-based sealant. The use of protecting groups for amino acids, such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, isocyanate, or aldehyde groups on the benefit agent for coupling to the hair-binding or skin binding peptide. These modifications may be done using routine chemistry such as oxidation, reduction, phosgenation, and the like, which is well known in the art.

It may also be desirable to couple the shampoo-resistant hair-binding peptide to the hair conditioning agent via a spacer. The spacer serves to separate the conditioning agent from the peptide to ensure that the agent does not interfere with the binding of the peptide to the hair. The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The spacer may be covalently attached to the peptide and the benefit agent using any of the coupling chemistries described above. In order to facilitate incorporation of the spacer, a bifunctional cross-linking agent that contains a spacer and reactive groups at both ends for coupling to the peptide and the benefit agent may be used.

Additionally, the spacer may be a peptide comprising any amino acid and mixtures thereof. The preferred peptide spacers are comprised of the amino acids proline, lysine, glycine, alanine, and serine, and mixtures thereof. In addition, the peptide spacer may contain a specific enzyme cleavage site, such as the protease Caspase 3 site, given as SEQ ID NO:9, which allows for the enzymatic removal of the benefit agent from the hair. The peptide spacer may be from 1 to about 50 amino acids, preferably from 1 to about 20 amino acids in length. Exemplary peptide spacers include, but are not limited, to SEQ ID NOs:10-12. These peptide spacers may be linked to the binding peptide sequence by any method known in the art. For example, the entire binding peptide-peptide spacer diblock may be prepared using the standard peptide synthesis methods described supra. In addition, the binding peptide and peptide spacer blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides. Alternatively, the entire binding peptide-peptide spacer diblock may be prepared using the recombinant DNA and molecular cloning techniques described supra. The spacer may also be a combination of a peptide spacer and an organic spacer molecule, which may be prepared using the methods described above.

It may also be desirable to have multiple shampoo-resistant hair-binding peptides coupled to the hair conditioning agent to enhance the interaction between the peptide-based hair conditioner and the hair, as described above. Either multiple copies of the same shampoo resistant hair-binding peptide or a combination of different shampoo-resistant hair-binding peptides may be used. The multi-copy shampoo resistant hair-binding peptide may comprise various spacers as described above. In the case of large conditioning particles (e.g., particle emulsions or nanopartilces), a large number of hair-binding peptides, i.e., up to about 50,000, may be coupled to the conditioning agent. A smaller number of hair-binding peptides can be coupled to the smaller conditioner molecules, i.e., up to about 100. Additionally, multiple peptide sequences may be linked together and attached to the conditioning agent. Therefore, in one embodiment of the present invention, the peptide-based hair conditioners are diblock compositions consisting of a shampoo-resistant hair-binding peptide (SRHBP) and a hair conditioning agent (HCA), having the general structure $(SRHBP_m)_n$-HCA, where m ranges from ranges from 1 to about 100, preferably from 1 to about 10. When the hair conditioning agent is a molecular species, i.e., a non-particle conditioning agent, n ranges from 1 to about 100, preferably from 1 to about 10. When the hair conditioning agent is a particle, n ranges from 1 to about 50,000, preferably from 1 to about 10,000.

In another embodiment, the peptide-based hair conditioners contain a spacer (S) separating the shampoo-resistant hair-binding peptide from the hair conditioning agent, as described above. Multiple copies of the shampoo resistant hair-binding peptide may be coupled to a single spacer molecule. Additionally, multiple copies of the peptides may be linked together via spacers and coupled to the hair conditioning agent via a spacer. In this embodiment, the peptide-based hair conditioners are triblock compositions consisting of a shampoo-resistant hair-binding peptide, a spacer, and a hair conditioning agent, having the general structure $[(SRHBP)_x\text{-}S_m]_n\text{-}HCA$, where x ranges from 1 to about 10, preferably x is 1, and m ranges from 1 to about 100, preferably from 1 to about 10. When the hair conditioning agent is a molecular species, i.e., a non-particle conditioning agent, n ranges from 1 to about 100, preferably from 1 to about 10. When the hair conditioning agent is a particle, n ranges from 1 to about 50,000, preferably from 1 to about 10,000.

The peptide-based hair conditioners of the present invention may be used in products for hair care. It should also be recognized that the shampoo-resistant hair-binding peptides themselves may serve as conditioning agents for the treatment of hair. Hair care product compositions are herein defined as compositions for the treatment of hair, including but not limited to shampoos, conditioners, lotions, aerosols, gels, mousses, and hair dyes comprising an effective amount of a peptide-based hair conditioner or a mixture of different peptide-based hair conditioners in a cosmetically acceptable medium. An effective amount of a peptide-based hair conditioner or hair-binding peptide for use in a hair care product composition is herein defined as a proportion of from about 0.01% to about 10%, preferably about 0.01% to about 5% by weight relative to the total weight of the composition. Components of a cosmetically acceptable medium for hair care product compositions are well-known in the art and examples are described by Philippe et al. in U.S. Pat. No. 6,280,747, Omura et al. in U.S. Pat. No. 6,139,851 and Cannell et al. in U.S. Pat. No. 6,013,250.

In one embodiment, the shampoo-resistant peptide-based hair conditioners of the invention are used in a shampoo composition. Suitable hair shampoo product compositions are well known in the art. Components of hair shampoo product compositions are described by Wells et al. in U.S. Pat. No. 6,930,078, and by Patel et al. in U.S. Pat. No. 5,747,436 and Niemiec et al. in U.S. Pat. No. 6,908,889, all of which are incorporated herein by reference. For example, the hair shampoo composition can be an aqueous solution, aqueous-alcoholic solution or an oil-in-water (O/W) or water in oil in water (W/O/W) emulsion. The shampoo composition of the invention typically contains an amount of peptide-based hair conditioner from about 0.01% to about 10%, additionally from about 0.01% to about 5%, and additionally about 0.5%, based on the total weight of the composition. The balance of the shampoo composition is comprised of the fluid vehicle and other additives. Typically, the fluid vehicle comprises water and other solvents which can include, without limitation, mineral oils and fatty alcohols.

Surfactants are the primary components in shampoo compositions. The amount of primary surfactant is generally in the range of between about 10% and 20% as based on the final weight of the composition, more typically from about 8 to about 18%. A secondary surfactant may also be present, generally in the range of about 0 to about 6%. The surfactants in the shampoo composition according to the invention may include one or more, or a combination thereof of anionic, nonionic, amphoteric or cationic surfactants. Examples of anionic surfactants include, but are not limited to, soaps, alkyl and alkyl ether sulfates, and alpha-olefin sulfonates. The preferred anionic surfactants are lauryl (ammonium, sodium, triethanolamine and diethanolamine and laureth (sodium and ammonium) sulfates. Secondary anionic surfactants include, but are not limited to, sulfosuccinates, linear alkylbenzene sulfonates, N-acyl methyltaurates, N-acyl sarcosinates, acyl isethionates, N-acyl polypeptide condensates, polyalkoxylated ether glycolates, monoglyceride sulfates, fatty glycerol ether sulfonates. Examples of nonionic surfactants include, but are not limited to, fatty alkanolamides, amine oxides, polymeric ethers, polysorbate 20, PEG-80 sorbitan, and nonoxynols. Examples of amphoteric surfactants include, but are not limited to, betaines, alkyl-substituted amino acids (sodium lauraminopropionate and sodium lauriminopropionate).

The shampoo composition according to the invention may also comprise viscosity and foam stabilizers, the amount of, generally in the range of about 1.5 to about 5% based on the final weight of the composition. Specific examples of viscosity/foam stabilizers include, but are not limited to, alkanolamides (i.e. Cocamide MEA).

Additionally, the shampoo composition may contain minor proportions of one or more conventional cosmetic or dermatological additives or adjuvants, provided that they do not interfere with the mildness, performance or aesthetic characteristics desired in the final products. The total concentration of added ingredients usually is less than 5%, preferably less than 3%, by weight of the total composition. Such minor components include but are not limited to, opacifying/pearlizing agents, such as stearic acid derivatives (e.g., ethylene glycol monostearate or ethylene glycol distearate); solvents; sequestering agents, such as disodium ethylene diaminetetraacetic acid (EDTA) and its salts, citric acid, or polyphosphates; stabilizing agents; viscosifying agents, such as salts (e.g, sodium chloride or ammonium chloride) for anionic formulations; PEG-120 methyl glucose dioleate and PEG-150 pentaerythrityl tetrastearate for anionic/nonionic formulations; hair conditioning agents, such as the cationic polymers polyquaternium 10 (Ucare Polymers), cationic guar (Jacquar C-261 N), polyquaternium-7 (Merquat Polymers) and silicones such as dimethicone and aminodimethicone; humectants; anti-static agents; anti-freezing agents, buffering agents; antioxidants, such as BHT, BHA and tocopherol; UV absorbers, such as benzophenone; preservatives, such as parabens; fragrances; and dyes or pigments. These adjuvants are well known in the field of cosmetics and are described in many publications, for example see *Harry's Book of Cosmeticology*, 8$^{th}$ edition, Martin Rieger, ed., Chemical Publishing, New York (2000).

The final essential component in the shampoo composition is water, which provides an aqueous medium that constitutes the balance of the shampoo composition. Generally, the proportion of water will range from about 53% to about 95%, preferably, 68% to about 92%, and most preferably about 80% to about 87%, by weight of the resultant shampoo composition.

The shampoo compositions of the present invention may be prepared using conventional formulation and mixing techniques. Where melting or dissolution of solid surfactants or wax components is required these can be added to a premix of the surfactants, or some portion of the surfactants, mixed and heated to melt the solid components, e.g., about 72° C. This mixture can then optionally be processed through a high shear mill and cooled, and then the remaining components are mixed in. The compositions typically have a final viscosity of from about 2,000 to about 20,000 cps (centipoise). The viscosity of the composition may be adjusted by conventional techniques including addition of sodium chloride or ammonium xylenesulfonate as needed.

Peptide-Based Hair Colorants

The peptide-based hair colorants of the invention are formed by coupling a shampoo-resistant hair-binding peptide (SRHBP) with a coloring agent (C). The shampoo-resistant hair-binding peptide part of the peptide-based hair colorant binds strongly to the hair and is not removed by the application of a shampoo, thus keeping the coloring agent attached to the hair for a long lasting hair coloring effect. The shampoo-resistant hair-binding peptides are selected by the methods described and include, but are not limited to, the hair-binding peptide sequences given as SEQ ID NOs:1-8.

Coloring agents as herein defined are any dye, pigment, and the like that may be used to change the color of hair. In the peptide-based hair colorants of the present invention, any suitable coloring agent may be used. Hair coloring agents are well known in the art (see for example Green et al. supra, *CFTA International Color Handbook*, $2^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany). Suitable hair coloring agents include, but are not limited to dyes, such as 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse Violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, zinc oxide, barium oxide, ultramarine blue, bismuth citrate, and carbon black particles. Carbon nanotubes may also be used as a black pigment for dyeing hair, as described by Huang et al. in copending and commonly owned U.S. patent application Ser. Nos. 11/093,873 and 11/093,533. The preferred hair coloring agents of the present invention are D&C Yellow 1 and 3, HC Yellow 6 and 8, D&C Blue 1, HC Blue 1, HC Brown 2, HC Red 5,2-nitro-paraphenylenediamine, N,N-hydroxyethyl-2-nitro-phenylenediamine, titanium dioxide, 4-nitro-indole, iron oxides, carbon black, and carbon nanotubes.

Metallic and semiconductor nanoparticles may also be used as hair coloring agents due to their strong emission of light (Vic et al. U.S. Patent Application Publication No. 2004/0010864). The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc oxide, zinc sulfide, zinc selenide, lead sulfide, gallium arsenide, silicon, tin oxide, iron oxide, and indium phosphide. The nanoparticles are stabilized and made water-soluble by the use of a suitable organic coating or monolayer. As used herein, monolayer-protected nanoparticles are one type of stabilized nanoparticle. Methods for the preparation of stabilized, water-soluble metal and semiconductor nanoparticles are known in the art, and are described by Huang et al. in copending U.S. patent application Ser. No. 10/622,889 and U.S. Patent Application Publication No. 2004/0115345, which are incorporated herein by reference. The color of the nanoparticles depends on the size of the particles. Therefore, by controlling the size of the nanoparticles, different colors may be obtained. For example, ZnS-coated CdSe nanoparticles cover the entire visible spectrum over a particle size range of 2 to 6 nm. Specifically, CdSe nanoparticles with a core size of 2.3, 4.2, 4.8 and 5.5 nm emit light at the wavelength centered around 485, 565, 590, and 625 nm, respectively. Water-soluble nanoparticles of different sizes may be obtained from a broad size distribution of nanoparticles using the size fractionation method described by Huang et al. (U.S. patent application Ser. No. 10/622,889 and U.S. Patent Application Publication No. 2004/0115345). The method described therein comprises the regulated addition of a water-miscible organic solvent to a solution of nanoparticles in the presence of an electrolyte. Increasing additions of the water-miscible organic solvent result in the precipitation of nanoparticles of decreasing size. The metallic and semiconductor nanoparticles may also serve as voluminizing agents, as described above.

Additionally, organic and inorganic nanoparticles, having an attached, adsorbed, or absorbed dye, may be used as a hair coloring agent. For example, the hair coloring agent may be colored polymer nanoparticles. Exemplary polymer nanoparticles include, but are not limited to, microspheres comprised of materials such as polystyrene, polymethylmethacrylate, polyvinyltoluene, styrene/butadiene copolymer, and latex. For use in the invention, the microspheres have a diameter of about 10 nanometers to about 2 microns. The microspheres may be colored by coupling any suitable dye, such as those described above, to the microspheres. The dyes may be coupled to the surface of the microsphere or adsorbed within the porous structure of a porous microsphere. Suitable microspheres, including undyed and dyed microspheres that are functionalized to enable covalent attachment, are available from companies such as Bang Laboratories (Fishers, Ind.).

The peptide-based hair colorants of the present invention are prepared by coupling a specific shampoo-resistant hair-binding peptide to a coloring agent, either directly or via a spacer. Any of the coupling methods described above may be used. It may be necessary to introduce reactive groups, such as carboxylic acid, alcohol, amine, aldehyde, or isocyanate groups, on the coloring agent for coupling to the hair-binding peptide. These modifications may be done using routine chemistry, which is well known in the art. For example, the surface of carbon black particles may be oxidized using nitric acid, a peroxide such as hydrogen peroxide, or an inorganic initiator such as ammonium persulfate, to generate functional groups. Preferably, the carbon black surface is oxidized using ammonium persulfate as described by Carrasco-Marin et al. (*J. Chem. Soc., Faraday Trans.* 93:2211-2215 (1997)). Amino functional groups may be introduced to the surface of carbon black using an organic initiator such as 2,2'-Azobis(2-methylpropionamide)-dihydrochloride. The inorganic pigments and the nanoparticles may be derivatized to introduce carboxylic acid or amino functional groups in a similar manner.

It may also be desirable to have multiple shampoo-resistant hair-binding peptides coupled to the coloring agent to enhance the interaction between the peptide-based hair colorant and the hair, as described above. Either multiple copies of the same shampoo resistant hair-binding peptide or a combination of different shampoo resistant hair-binding peptides may be used. In the case of large pigment particles, a large number of shampoo resistant hair-binding peptides, i.e., up to about 50,000, may be coupled to the pigment. A smaller number of shampoo resistant hair-binding peptides can be coupled to the smaller dye molecules, i.e., up to about 100. Additionally, multiple peptide sequences may be linked together and attached to the coloring agent, as described above. Therefore, in one embodiment of the present invention, the peptide-based hair colorants are diblock compositions consisting of a shampoo-resistant hair-binding peptide (SRHBP) and a coloring agent (C), having the general structure $(SRHBP_m)_n$-C, where m ranges from ranges from 1 to about 100, preferably from 1 to about 10. When the coloring agent is a molecular species, such as a dye, n ranges from 1 to about 100, preferably from 1 to about 10. When the coloring agent is a particle, such as a pigment or nanoparticle, n ranges from 1 to about 50,000, preferably from 1 to about 10,000.

In another embodiment, the peptide-based hair colorants contain a spacer (S) separating the binding peptide from the hair coloring agent, as described above. Multiple copies of the shampoo-resistant hair-binding peptide may be coupled to a single spacer molecule. Additionally, multiple copies of the peptides may be linked together via spacers and coupled to the coloring agent via a spacer. In this embodiment, the peptide-based hair colorants are triblock compositions consisting of a shampoo-resistant hair-binding peptide, a spacer, and a coloring agent, having the general structure $[(SRHBP)_x\text{-}S_m]_n$-C, where x ranges from 1 to about 10, preferably x is 1, and m ranges from 1 to about 100, preferably from 1 to about 10. When the coloring agent is a molecular species, such as a dye, n ranges from 1 to about 100, preferably from 1 to about 10. When the coloring agent is a particle, such as a pigment or nanoparticle, n ranges from 1 to about 50,000, preferably from 1 to about 10,000.

The peptide-based hair colorants of the present invention may be used in hair coloring products for dyeing hair. Hair coloring product compositions are herein defined as compositions for the coloring, dyeing, or bleaching of hair, comprising an effective amount of peptide-based hair colorant or a mixture of different peptide-based hair colorants in a cosmetically acceptable medium. An effective amount of a peptide-based hair colorant for use in a hair coloring product composition is herein defined as a proportion of from about 0.001% to about 20% by weight relative to the total weight of the composition. Components of a cosmetically acceptable medium for hair coloring product compositions are described by Dias et al., in U.S. Pat. No. 6,398,821 and by Deutz et al., in U.S. Pat. No. 6,129,770, both of which are incorporated herein by reference. For example, hair coloring product compositions may contain sequestrants, stabilizers, thickeners, buffers, carriers, surfactants, solvents, antioxidants, polymers, and conditioners. The conditioners may include the peptide-based hair conditioners and shampoo-resistant hair-binding peptides of the present invention in a proportion from about 0.01% to about 10%, preferably about 0.01% to about 5% by weight relative to the total weight of the hair coloring composition.

In one embodiment, the shampoo-resistant peptide-based hair colorants of the invention are used in a shampoo composition. Components of shampoo compositions are described above.

The peptide-based hair colorants of the present invention may also be used as coloring agents in cosmetic compositions that are applied to the eyelashes or eyebrows including, but not limited to mascaras, and eyebrow pencils. These may be anhydrous make-up products comprising a cosmetically acceptable medium which contains a fatty substance in a proportion generally of from about 10 to about 90% by weight relative to the total weight of the composition, where the fatty phase containing at least one liquid, solid or semi-solid fatty substance, as described above. The fatty substance includes, but is not limited to, oils, waxes, gums, and so-called pasty fatty substances. Alternatively, these compositions may be in the form of a stable dispersion such as a water-in-oil or oil-in-water emulsion, as described above. In these compositions, the proportion of the peptide-based hair colorant is generally from about 0.001% to about 20% by weight relative to the total weight of the composition.

Methods for Treating Hair

In another embodiment, methods are provided for treating hair with the shampoo-resistant peptide-based conditioners and colorants of the present invention. Specifically, the present invention also comprises a method for forming a protective film of shampoo-resistant peptide-based conditioner on hair by applying one of the compositions described above comprising an effective amount of a peptide-based hair conditioner to the hair and allowing the formation of the protective film. The compositions of the present invention may be applied to the hair by various means, including, but not limited to, spraying, brushing, and applying by hand. The peptide-based conditioner composition is left in contact with the hair for a period of time sufficient to form the protective film, preferably for at least about 0.1 to 60 min.

The present invention also provides a method for coloring hair by applying a hair coloring composition comprising an effective amount of a shampoo-resistant peptide-based hair colorant to the hair by means described above. The hair coloring composition is allowed to contact the hair for a period of time sufficient to cause coloration of the hair, preferably between about 5 to about 50 min, and then the hair coloring composition may be rinsed from the hair.

The present invention also provides a method for coloring eyebrows and eyelashes by applying a cosmetic composition comprising an effective amount of a peptide-based hair colorant to the eyebrows and eyelashes using the methods described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "pfu" means plague forming unit, "bp" means base pair(s), "BSA" means bovine serum albumin, "ELISA" means enzyme linked immunosorbent assay, "A" means absorbance, "$A_{450}$" means the absorbance measured at a wavelength of 450 nm, "TBS" means Tris-buffered saline, "TBST-X" means Tris-buffered saline containing Tween® 20 where "X" is the weight percent of Tween® 20, "SEM" means standard error of the mean, "DMF" means dimethylformamide, "TH F" means tetrahydrofuran, "NM R" means nuclear magnetic resonance spectroscopy, "LC-MS" means liquid chromatography-mass spectrometry, "MALDI mass spectrometry" means matrix assisted laser desorption ionization mass spectrometry, "EDTA" means ethylenediamine tetraacetate, "qs" means as much as suffices.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in Biotechnology. A Textbook of Industrial Microbiology, Second Edition, Sinauer Associates, Inc., Sunderland, Mass., 1989. All reagents and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Phase Display Peptide Libraries:

Four phage display peptide libraries were used in the following Examples. The Ph.D.-12™ Phage Display Peptide Library Kit and Ph.D.-7™ Phage Display Library Kit, were purchased from New England BioLabs (Beverly, Mass.). These kits are based on a combinatorial library of random peptide 7 or 12-mers fused to a minor coat protein (pIII) of M13 phage. The displayed peptide is expressed at the N-terminus of pIII, such that after the signal peptide is cleaved, the first residue of the coat protein is the first residue of the displayed peptide. The Ph.D.-7 and Ph.D.-12 libraries consist of approximately $2.8 \times 10^9$ and $2.7 \times 10^9$ sequences, respectively.

Two other phage display peptide libraries, one containing 15-mer random peptide sequences and the other containing 20-mer random peptide sequences, were prepared using the method described by Scholle et al. (*Combinatorial Chemistry & High Throughput Screening*, 8:545-551 (2005)). This method is a modification of the method reported by Sidhu et al. (*Methods in Enzymology* 328:333-363 (2000)) in which *E. coli* strain CJ236 (dut⁻ ung⁻) is used to generate uridine-containing single-stranded phagemid DNA (U-ssDNA). This DNA is used as a template for second-strand synthesis using an oligonucleotide, not only as a primer of the second strand, but also to insert encoding random amino acids. Upon completion of second strand synthesis, the double stranded DNA is transformed into a wild-type strain. Any U-ssDNA is degraded by the host cell, thus leaving only the recombinant strand to generate phage particles. This method can be utilized to generate peptide fusions or mutations to the M13 coat proteins. The method of Kay et al. uses an amber stop codon at beginning of gene III. Oligonucleotides containing randomized stretches of DNA sequence are annealed to the single-stranded phage genome, such that the randomized region aligns with the stop codon. The ssDNA is enzymatically converted to covalently-closed, circular dsDNA and subsequently electroporated into a non-suppressor strain of *E. coli*. The newly synthesized DNA strand (minus strand) serves as the template for generation of the plus strand in the host cell, which is utilized for transcription/translation of viral genes and is packaged into the virus particle.

The titers for the resulting 15-mer and 20-mer libraries were $4.1 \times 10^{12}$ pfu/mL and $4.2 \times 10^{12}$ pfu/mL, respectively.

Example 1

Identification of Shampoo-Resistant Hair-Binding Phage-Peptides Using Biopanning The purpose of this Example was to identify shampoo-resistant hair-binding phage-peptides using a modified biopanning procedure, wherein the phage-peptide-hair complexes are contacted with different dilutions of a shampoo product.

The samples used as normal hair were 6-inch medium brown human hairs obtained from International Hair Importers and Products (Bellerose, N.Y.). The hairs were placed in 90% isopropanol for 30 min at room temperature and then washed 5 times for 10 min each with deionized water. The hairs were air-dried overnight at room temperature.

To prepare the bleached hair samples, the medium brown human hairs were placed in 6% $H_2O_2$, which was adjusted to pH 10.2 with ammonium hydroxide, for 10 min at room temperature and then washed 5 times for 10 min each with deionized water. The hairs were air-dried overnight at room temperature.

The normal and bleached hair samples were cut into 0.5 to 1 cm lengths and about 5 to 10 mg of the hairs was placed into wells of a custom 24-well biopanning apparatus that had a pig skin bottom. An equal number of the pig skin bottom wells were left empty. The pig skin bottom apparatus was used as a subtractive procedure to remove phage-peptides that have an affinity for skin. This apparatus was created by modifying a dot blot apparatus (obtained from Schleicher & Schuell, Keene, N.H.) to fit the biopanning process. Specifically, the top 96-well block of the dot blot apparatus was replaced by a 24-well block. A 4×6 inch treated pig skin was placed under the 24-well block and panning wells with a pig skin bottom were formed by tightening the apparatus. The pig skin was purchased from a local supermarket and stored at −80° C. Before use, the skin was placed in deionized water to thaw, and then blotted dry using a paper towel. The surface of the skin was wiped with 90% isopropanol, and then rinsed with deionized water. The 24-well apparatus was filled with blocking buffer consisting of 1 mg/mL BSA in TBST containing 0.5% Tween® 20 (TBST-0.5%) and incubated for 1 h at 4° C. The wells and hairs were washed 5 times with TBST-0.5%. One milliliter of TBST-0.5% containing 1 mg/mL BSA was added to each well. Then, 10 µL of the original 12-mer phage library ($2\times10^{11}$ pfu), was added to the pig skin bottom wells that did not contain a hair sample and the phage library was incubated for 15 min at room temperature. The unbound phages were then transferred to pig skin bottom wells containing the hair samples and were incubated for 15 min at room temperature. The phage-peptide-complexed hairs were placed in separate tubes and contacted with 10%, 30% and 50% shampoo solutions (Pantene Pro-V shampoo, Sheer Volume, Proctor & Gamble, Cincinnati, Ohio) for 5 min, followed by six TBS buffer washes. The hairs, which had shampoo-resistant phage peptides still attached, were used to directly infect 500 μL of mid-log phase bacterial host cells, *E. coli* ER2738 (New England BioLabs), which were then grown in LB medium for 20 min and then mixed with 3 mL of agarose top (LB medium with 5 mM $MgCl_2$, and 0.7% agarose) at 45° C. This mixture was spread onto a LB medium/IPTG/S-Gal™ plate (LB medium with 15 g/L agar, 0.05 g/L IPTG, and 0.04 g/L S-Gal™) and incubated overnight at 37° C. The black plaques were counted to calculate the phage titer. The single black plaques were randomly picked and were prepared following the manufacturer's instructions (New England Labs). The single stranded phage genomic DNA was purified using the QIAprep Spin M13 Kit (Qiagen, Valencia, Calif.) and sequenced at the DuPont Sequencing Facility using −96 gIII sequencing primer (5'-CCCTCAT-AGTTAGCGTAACG-3'), given as SEQ ID NO:13. The displayed peptide is located immediately after the signal peptide of gene III.

A potential problem with this method is the effect of the shampoo on the phage's ability to infect bacterial host cells. In a control experiment, a known amount of phage particles was added to a 10% shampoo solution for 5 min, and then a portion of the solution was used to infect bacterial cells. The titer of the shampoo-treated phage was 90% lower than that of the untreated phage. The 30% and 50% shampoo treatments more severely damaged the phage's ability to infect host cells. Nevertheless, two shampoo-resistant hair-binding phage-peptides were identified, as shown in Table 1.

TABLE 1

Peptide Sequences of Shampoo-Resistant Hair-binding Phage Peptides Identified Using the Biopanning Method

| Clone | Sequence | Target | SEQ ID NO: |
|---|---|---|---|
| I-B5 | TPPELLHGDPRS | Normal and Bleached Hair | 1 |
| H-B1 | TPPTNVLMLATK | Normal Hair | 2 |

Example 2

Identification of Shampoo-Resistant Hair-Binding Phage-Peptides Using PCR

The purpose of this Example was to identify shampoo-resistant hair-binding phage-peptides using a PCR method to avoid the problem of shampoo induced damage to the phage. The principle of the PCR method is that DNA fragments inside the phage particle can be recovered using PCR, regardless of the phage's viability, and that the recovered DNA fragments, corresponding to the hair-binding peptide sequences, can then been cloned back into a phage vector and packaged into healthy phage particles.

Biopanning experiments were performed using 7-mer and 12-mer phage-peptide libraries against normal and bleached hairs, using the procedure described in Example 1. After the final wash, the phage-treated hairs were contacted with diluted shampoo for 5 min, as described in Example 1, followed by six TBS buffer washes. The shampoo-treated hairs were put into a new tube filled with 1 mL of water, and boiled for 15 min to release the DNA. This DNA-containing, boiled solution was used as a DNA template for PCR reactions. The primers used in the PCR reaction were primers: M13KE-1412 Forward 5'-CAAGCCTCAGCGACCGAATA-3', given as SEQ ID NO:14 and M13KE-1794 Reverse 5'-CGTAA-CACTGAGTTTCGTCACCA-3', given SEQ ID NO:15. The PCR conditions were: 3 min denaturing at 96° C., followed by 35 cycles of 94° C. for 30 sec, 50° C. for 30 sec and 60° C. for 2 min. The PCR products (~400 bp), and M13KE vector (New England BioLabs) were digested with restriction enzymes Eag I and Acc65 I. The ligation and transformation conditions, as described in the Ph.D.™ Peptide Display Cloning System (New England Biolabs), were used. The amino acid sequence of the resulting shampoo-resistant hair-binding phage-peptide is NTSQLST, given as SEQ ID NO:3.

Example 3

Identification of Shampoo and Hair Conditioner-Resistant Hair-Binding Peptides

The purpose of this Example was identify shampoo and hair conditioner-resistant hair-binding peptides from three random phage display peptide libraries.

The hair samples used were 6-inch (15 cm) long pieces of 90% gray human hairs, obtained from International Hair Importers and Products (Bellerose, N.Y.). The hairs were placed in 90% isopropanol for 30 min at room temperature and then washed 5 times for 10 min each with deionized water. The hairs were air-dried overnight at room temperature. Three hair bundles, representing root, middle, and tip, were prepared by cutting the gray hair in 1-cm lengths. The hairs were taped with 3M medical tape at one end, 100 hair fibers per bundle. The three bundles of hair were than treated with SuperBlocker (Pierce) at room temperature for 1 h, followed by 6 washes with TBST-0.1% (pH 7.2).

The phage libraries, pre-absorbed as described above to remove skin and plastic-binding clones, were mixed in 1:1 ratio with Clean Replenishing® Conditioner (Neutrogena Corp., Los Angeles, Calif.). The conditioner and pre-adsorbed phage library mixtures were added to a tube containing the hair bundles and were incubated at 37° C. for 15 min with gentle shaking. The hair bundles were transferred into new 15-mL tubes and were washed 6 times (10 mL/each) with TBST-0.5% (adjusted to pH 5.0 with HCl). The hair bundles were then immersed in Clean Replenishing® Shampoo (Neutrogena Corp., Los Angeles, Calif.) for 5 min at 37° C., followed by 6 washes with TBST-0.5% Tween 20. The taped ends of the hair bundles were then cut off and transferred to 1.5-mL centrifuge tubes. Elution buffer, consisting of 1 mg/of BSA in 0.2 M glycine-HCl, pH 2.2, was added, and the hair was incubated for 10 min. Then, neutralization buffer consisting of 1 M Tris-HCl, pH 9.2, was added to the tube. The phages that were eluted and those still bound to the hairs were amplified by adding fresh host cells *E. coli* ER2338. The amplified and isolated phages were contacted with a fresh hair sample and the biopanning procedure described above was repeated two more times with each library.

After the third biopanning round, random single phage clones were selected and single plaque lysates were prepared following the manufacture's instructions (New England BioLabs) and the single stranded phage genomic DNA was purified using the QIAprep Spin M13 Kit (Qiagen; Valencia, Calif.) and sequenced as described in Example 1. The displayed peptide is located immediately after the signal peptide of gene III. The amino acid sequences of the hair conditioner-resistant, hair-binding phage-peptides, identified from the three phage libraries after three biopanning rounds, are given in Table 2.

TABLE 2

Amino Acid Seauences of Shampoo and Conditioner-Resistant Hair-binding Phacie Peptides

| Clones | Sequences | Target | SEQ ID No: |
|---|---|---|---|
| Gray 1 | GMPAMHWIHPFA | Gray hair | 5 |
| Gray 3 | HDHKNQKETHQRHAA | Gray hair | 6 |
| Gray 4 | HNHMQERYTDPQHSPSVNGL | Gray hair | 7 |
| Gray 5 | TAEIQSSKNPNPHPQRSWTN | Gray hair | 8 |

Example 4

Preparation of a Shampoo-Resistant Peptide-Based Hair Colorant

The purpose of this Example was to prepare a peptide-based hair colorant by covalently attaching the shampoo-resistant IB5 hair-binding peptide having an added cysteine residue on the C-terminal end (SEQ ID NO:4) to Disperse Orange 3 dye. The dye was first functionalized with isocyanate and then reacted with the peptide.

Functionalization of Disperse Orange 3:

In a dry box, 14.25 g of Disperse Orange 3 (Aldrich) was suspended in 400 mL of dry THF (tetrahydrofuran) in an addition funnel. A 2-L, four-neck reaction flask (Corning Inc., Corning, N.Y.; part no. 1533-12), containing a magnetic stir bar, was charged with 200 mL of dry toluene. The flask was fitted with a cold finger condenser (Corning Inc., part no. 1209-04) and with a second cold finger condenser with an addition funnel, and was placed on an oil bath in a hood.

Phosgene (25.4 mL) was condensed into the reaction flask at room temperature. After phosgene addition was complete, the temperature of the oil bath was raised to 80° C. and the Disperse Orange 3 suspension was added to the reaction flask dropwise in 100 mL increments over 2 h, while monitoring the reaction temperature and gas discharge from the scrubber. The temperature was maintained at or below 64° C. throughout the addition. After addition was complete, the reactants were heated at 64° C. for 1 h and then allowed to cool to room temperature with stirring overnight.

The reaction solvents were vacuum-distilled to dryness, while maintaining the contents at or below 40° C., and vacuum was maintained for an additional hour. The reaction flask was transferred to a dry box; the product was collected and dried overnight (15.65 g). The desired product was confirmed by proton NMR.

Coupling of Isocyanate-Functionalized Disperse Orange 3 with IB5 Hair-Binding Peptide:

Isocyanate-functionalized Disperse Orange 3 [(2-(4-isocyantophenyl)-1-(4-nitrophenyl)diazene](27 mg), prepared as described above, was dissolved in 5 mL of DMF. The IB5 peptide having a cysteine residue added to the C-terminus (100 mg), given as SEQ ID NO:4, was dissolved in 10 mL of DMF and the resulting solution was added to the functionalized Disperse Orange 3 solution. Two drops of triethylamine were added to the solution and the solution was stirred at room temperature for 3 days. The solvent was evaporated, yielding 110 mg of a purplish solid. The product was analyzed by MALDI mass spectrometry, which confirmed that the primary product formed was the peptide covalently coupled to the dye.

Example 5

Shampoo Composition Comprising a Shampoo-Resistant Peptide-Based Hair Colorant

The purpose of this prophetic Example is to describe the preparation of a coloring shampoo composition comprising a peptide-based hair colorant in a shampoo matrix.

The coloring shampoo composition is prepared using the ingredients listed in Table 3.

TABLE 3

| Coloring Shampoo Composition | |
|---|---|
| Ingredient | Wt % |
| Ammonium Laureth Sulfate | 12 |
| Sodium Laureth Sulfate | 5 |
| Dihydrogenated tallow phthalic acid amide | 4 |
| Cocamide MEA | 2 |
| Polyquaternium-10 | 1 |
| Peptide-based hair colorant from Example 4 | 0.5 |
| Citric acid | to adjust pH |
| Disodium EDTA | 0.5 |
| Fragrance | 0.7 |
| Water | qs to 100 |

The shampoo composition is prepared by combining water and the EDTA, heating to 65° C. and mixing until the EDTA is dissolved. Then the remaining ingredients are added, and the mixture is mixed until all the solids are dissolved and the color is uniform. The pH is adjusted with citric acid as desired.

Example 6

Preparation of a Shampoo-Resistant Peptide-Based Hair Conditioner

The purpose of this Example was to prepare a peptide-based hair conditioner by coupling the shampoo-resistant peptide IB5 to an octadadecyl alkyl chain.

Octadecylisocyanate (70 mg, Aldrich, CAS No.112-96-9) was dissolved in 5 mL of N,N'-dimethylformamide (DMF) and was added to a solution of unprotected IB5 peptide having an added cysteine residue on the C-terminal end, TPPELLHGDPRSC, given as SEQ ID NO:4, (150 mg) dissolved in 10 mL of DMF. Triethylamine (30 mg) was added to catalyze the reaction. The solution was stirred at room temperature for 120 h. The solvent was evaporated yielding 191 mg of an off-white, crystalline powder. The product was analyzed by gas chromatography-MALDI mass spectrometry and found to contain two components having molecular weights of 1717 and 2013 g/mol, consistent with 1 and 2 octadecyl units respectively, covalently attached to the peptide.

Example 7

Shampoo Composition Comprising a Shampoo-Resistant Peptide-Based Hair Conditioner The purpose of this prophetic Example is to describe the preparation of a shampoo composition comprising a peptide-based hair conditioner in a shampoo matrix.

The conditioning shampoo composition is prepared using the ingredients listed in Table 4.

TABLE 4

Conditioning Shampoo Composition

| Ingredient | Wt % |
| --- | --- |
| Ammonium Laureth Sulfate | 12 |
| Sodium Laureth Sulfate | 5 |
| Dihydrogenated tallow phthalic acid amide | 4 |
| Cocamide MEA | 2 |
| Peptide-based hair conditioner from Example 6 | 1 |
| Citric acid | to adjust pH |
| Disodium EDTA | 0.5 |
| Fragrance | 0.7 |
| Water | qs to 100 |

The shampoo composition is prepared as described in Example 5.

What is claimed is:

1. A shampoo-resistant hair-binding peptide selected from the group consisting of SEQ ID NOs: 4, 5, 6, 7, and 8.

2. A diblock, peptide-based hair benefit agent having the general structure $(SRHBP_m)_n$-BA, wherein;
 a) SRHBP is the shampoo-resistant hair-binding peptide selected from the group consisting of SEQ ID NOs: 4, 5, 6, 7, and 8;
 b) BA is a benefit agent;
 c) m ranges from 1 to about 100; and
 d) n ranges from 1 to about 50,000.

3. A triblock, peptide-based hair benefit agent having the general structure $[(SRHBP)_x\text{-}S_m]_n$-BA, wherein;
 a) SRHBP is the shampoo-resistant hair-binding peptide selected from the group consisting of SEQ ID NOs: 4, 5, 6, 7, and 8;
 b) BA is a benefit agent;
 c) S is a spacer;
 d) x ranges from 1 to about 10;
 e) m ranges from 1 to about 100; and
 f) n ranges from 1 to about 50,000.

4. A diblock, peptide-based benefit agent according to claim 2 wherein the benefit agent is a hair conditioning agent.

5. A triblock, peptide-based benefit agent according to claim 3 wherein the benefit agent is a hair conditioning agent.

6. A diblock, peptide-based benefit agent according to claim 2 wherein the benefit agent is a coloring agent.

7. A triblock, peptide-based benefit agent according to claim 3 wherein the benefit agent is a coloring agent.

8. The peptide-based benefit agent of claim 4 or 5 wherein the hair conditioning agent is selected from the group consisting of octylamine, stearyl amine, behenyl alcohol, vinyl group terminated siloxanes, vinyl group terminated silicone, vinyl group terminated methyl vinyl siloxanes, vinyl group terminated methyl vinyl silicone, hydroxyl terminated siloxanes, hydroxyl terminated silicone, amino-modified silicone derivatives, [(aminoethyl)amino]propyl hydroxyl dimethyl siloxanes, [(aminoethyl)amino]propyl hydroxyl dimethyl silicones, alpha-tridecyl-omega-hydroxy-poly(oxy-1,2-ethanediyl), amodimethicone, and nanoparticles.

9. The peptide-based benefit agent of claim 6 or 7 wherein the coloring agent is selected from the group consisting of D&C Yellow 1, D&C Yellow 3, HC Yellow 6, HC Yellow 8, D&C Blue 1, HC Blue 1, HC Brown 2, HC Red 5, 2-nitro-paraphenylenediamine, N,N-hydroxyethyl-2-nitro-phenylenediamine, 4-nitro-indole, iron oxides, titanium dioxide, carbon black, carbon nanotubes, metal nanoparticles, semiconductor nanoparticles, and colored microspheres.

10. The peptide-based benefit agent of claim 9 wherein the colored microspheres are comprised of materials selected from the group consisting of polystyrene, polymethylmethacrylate, polyvinyltoluene, styrene/butadiene copolymer, and latex; and wherein the microspheres have a diameter of about 10 nanometers to about 2 microns.

11. The peptide-based benefit agent according to any of claims 3, 5, or 7 wherein the spacer is selected from the group consisting of ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl alkyl chain, propyl alkyl chain, hexyl alkyl chain, steryl alkyl chains, cetyl alkyl chains, and palmitoyl alkyl chains.

12. The peptide-based benefit agent according to any of claims 3, 5, or 7 wherein the spacer is a peptide comprising amino acids selected from the group consisting of proline, lysine, glycine, alanine, serine, and mixtures thereof.

13. The peptide-based benefit agent according to claim 12 wherein the spacer is a peptide comprising an amino acid sequence selected from the group consisting of SEQ ID NOs: 10, 11, and 12.

14. The peptide-based benefit agent according to claim 13 wherein the spacer optionally contains a cleavage site as set forth in SEQ ID NO:9.

15. A hair care product composition comprising an effective amount of the peptide-based benefit agent of claim 4 or 5.

16. A hair care product composition according to claim 15 wherein the product composition is a shampoo.

17. A hair coloring product composition comprising an effective amount of the peptide-based benefit agent of claim 6 or 7.

18. A hair coloring product composition according to claim 17 wherein the product composition is a shampoo.

19. A method for forming a protective layer of a peptide-based conditioner on hair comprising applying the composition of claim 15 or 16 to the hair and allowing the formation of said protective layer.

20. A method for coloring hair comprising applying the composition of claim 17 or 18 to the hair for a period of time sufficient to cause coloration of the hair.

21. A method for coloring hair, eyebrows or eyelashes comprising the steps of:
 a) providing a hair coloring composition comprising a hair colorant selected from the group consisting of:
  i) $(SRHBP_m)_n$-C; and
  ii) $[(SRHBP)_x\text{-}S_m]_n$-C
  wherein:
   1) SRHBP is the shampoo-resistant hair-binding peptide selected from the group consisting of SEQ ID NOs: 4, 5, 6, 7, and 8;
   2) C is a coloring agent;
   3) n ranges from 1 to about 50,000;
   4) S is a spacer;
   5) m ranges from 1 to about 100; and
   6) x ranges from 1 to about 10;
  and wherein the shampoo-resistant hair-binding peptide is selected by a method comprising the steps of:
   A) providing a combinatorial library of DNA associated peptides;
   B) contacting the library of (A) with a hair sample to form a reaction solution comprising DNA associated peptide-hair complexes;
   C) isolating the DNA associated peptide-hair complexes of (B) from the reaction solution;
   D) contacting the isolated DNA associated peptide-hair complexes of (C) with a shampoo matrix to form a peptide-hair complex-shampoo mixture wherein the concentration of the shampoo matrix is at least about 10% of the full strength concentration;

E) isolating the DNA associated peptide-hair complexes of (D) from the peptide-hair complex-shampoo mixture;

F) amplifying the DNA encoding the peptide portion of the DNA associated peptide-hair complexes of (E); and G) sequencing the amplified DNA of (F) encoding a shampoo-resistant hair-binding peptide wherein the shampoo-resistant hair-binding peptide is selected; and b) applying the hair coloring composition of (a) to hair, eyebrows or eyelashes for a time sufficient for the hair colorant to bind to hair, eyebrows or eyelashes.

22. A method for forming a protective layer of a peptide-based conditioner on hair comprising the steps of:

a) providing a hair care composition comprising a hair conditioner selected from the group consisting of:
   i) $(SRHBP_m)_n$-HCA; and
   ii) $[(SRHBP)_x-S_m]_n$-HCA
   wherein:
   1) SRHBP is the shampoo-resistant hair-binding peptide selected from the group consisting of SEQ ID NOs: 4, 5, 6, 7, and 8;
   2) HCA is a hair conditioning agent;
   3) n ranges from 1 to about 50,000;
   4) S is a spacer;
   5) m ranges from 1 to about 100; and
   6) x ranges from 1 to about 10;

and wherein the shampoo-resistant hair-binding peptide is selected by a method comprising the steps of:

A) providing a combinatorial library of DNA associated peptides;

B) contacting the library of (A) with a hair sample to form a reaction solution comprising DNA associated peptide-hair complexes;

C) isolating the DNA associated peptide-hair complexes of (B) from the reaction solution;

D) contacting the isolated DNA associated peptide-hair complexes of (C) with a shampoo matrix to form a peptide-hair complex-shampoo mixture wherein the concentration of the shampoo matrix is at least about 10% of the full strength concentration;

E) isolating the DNA associated peptide-hair complexes of (D) from the peptide-hair complex-shampoo mixture;

F) amplifying the DNA encoding the peptide portion of the DNA associated peptide-hair complexes of (E); and G) sequencing the amplified DNA of (F) encoding a shampoo-resistant hair-binding peptide wherein the shampoo-resistant hair-binding peptide is selected; and b) applying the hair care composition of (a) to hair and allowing the formation of said protective layer.

* * * * *